United States Patent
Goetzl

(10) Patent No.: US 10,393,760 B2
(45) Date of Patent: Aug. 27, 2019

(54) SPECIALIZED EXCITATORY SYNAPTIC PROTEIN BIOMARKERS OF PLASMA NEURONAL EXOSOMES FOR PREDICTION AND STAGING OF ALZHEIMER'S DISEASE

(71) Applicant: Edward J. Goetzl, San Francisco, CA (US)

(72) Inventor: Edward J. Goetzl, San Francisco, CA (US)

( * ) Notice: Subject to any disclaimer, the term of this patent is extended or adjusted under 35 U.S.C. 154(b) by 0 days.

(21) Appl. No.: 16/005,170

(22) Filed: Jun. 11, 2018

(65) Prior Publication Data

US 2019/0011460 A1 Jan. 10, 2019

Related U.S. Application Data

(60) Provisional application No. 62/528,567, filed on Jul. 5, 2017.

(51) Int. Cl.
*G01N 33/53* (2006.01)
*G01N 33/537* (2006.01)
*A01N 37/18* (2006.01)
*A61K 38/00* (2006.01)
*G01N 33/68* (2006.01)
*C12N 5/0793* (2010.01)

(52) U.S. Cl.
CPC ......... *G01N 33/6896* (2013.01); *C12N 5/062* (2013.01); *G01N 33/6842* (2013.01); *G01N 2800/28* (2013.01); *G01N 2800/2821* (2013.01); *G01N 2800/50* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| 2011/0269764 A1 | 11/2011 | Cohen et al. |
| 2015/0119278 A1 | 4/2015 | Goetzl |
| 2016/0327572 A1 | 11/2016 | Barnby et al. |

FOREIGN PATENT DOCUMENTS

| WO | 2016044697 A1 | 3/2016 |
| WO | 201600816 A1 | 12/2016 |

OTHER PUBLICATIONS

"Physical Basis of Cognitive Alterations in Alzheimer's Disease: Synapse Loss Is the Major Correlate of Cognitive Impairment", Ann. Neurol., Terry, Robert D. et al. (1991) 30, 572-580.
"Alzheimer's Disease Is a Synaptic Failure", Science, Selkoe, Dennis J. (Oct. 25, 2002) 298, 789-791.
"Synapse Loss in Frontal Cortex Biopsies in Alzheimer's Disease: Correlation with Cognitive Severity", Ann. Neural., DeKosky, Steven T. et al. (1990) 27, 457-464.
"Synapse Loss in Dementias", J. Neurosci. Res., Clare, Ryan et al. (Aug. 1, 2010) 88(10), 2083-2090.
"Decreased synaptic proteins in neuronal exosomes of frontotemporal dementia and Alzheimer's disease", Faseb J., Goetzl, Edward J. et al. (2016) 30, 4141-4148.
"Neuroligins and Neurexins Link Synaptic Function to Cognitive Disease", Nature, Sudhof, Thomas C. (Oct. 16, 2008) 455(7215), 903-911.
"The neurexin ligands, neuroligins and leucine-rich repeat transmembrane proteins, perform convergent and divergent synaptic functions in vivo", Proc. Natl. Acad. Sci. USA, Soler-Llavina, Gilberto J. et al. (Oct. 4, 2011) 108, 40, 16502-16509.
"Epigenetic suppression of neuroligin 1 underlies amyloid-induced memory deficiency", Nat. Neurosci., Bie, Bihua et al. (Feb. 2014) 17, 2, 223-231.
"Narp regulates homeostatic scaling of excitatory synapses on Parvalbumin interneurons", Nat. Neurosci., Chang, Michael C. et al. (Sep. 2010) 13(9), 1090-1097.
"2014 Update of the Alzheimer's Disease Neuroimaging Initiative: A review of papers published since its inception", Alzheimers Dement., Weiner, Michael W. et al. (Jun. 2015) 11(6), e1-120. [225 pages submitted in 6 parts due to size].
"Pentraxins Coordinate Excitatory Synapse Maturation and Circuit Integration of Parvalbumin Interneurons", Neuron, Pelkey, Kenneth A. et al. (May 4, 2016) 90, 661-664.
"Presynaptic Neuronal Pentraxin Receptor Organizes Excitatory and Inhibitory Synapses", J. Neurosci., Lee, Sung-Jin et al. (Feb. 1, 2017) 37(5), 1062-1080.

(Continued)

*Primary Examiner* — Olga N Chernyshev
(74) *Attorney, Agent, or Firm* — Breiner & Breiner, L.L.C.

(57) ABSTRACT

Combining presynaptic proteins, neuronal pentraxin 2 (NPTX2) and neurexin 2α (NRXN2α), with respective postsynaptic functional partners GluA4-containing glutamate receptor (AMPA4) and neuroligin 1 (NLGN1), and enhancing excitatory synaptic activities in areas of the hippocampus and cerebral cortex. As early damage of such excitatory circuits in Alzheimer's disease (AD) correlates with cognitive losses, plasma neuron-derived exosome (NDE) levels of these two pairs of synaptic proteins are quantified and serve as biomarkers. NDE contents of all four proteins decrease significantly in AD dementia and diminished levels of AMPA4 and NLGN1 correlate with the extent of cognitive losses. Prior to the onset of dementia, NDE levels of all but NPTX2 are significantly lower than those of matched control subjects and levels of all decline significantly with the development of dementia. Reductions in NDE levels of these excitatory synaptic proteins are indicators of cognitive losses and reflect progression of severity of AD.

2 Claims, 5 Drawing Sheets

(56) References Cited

OTHER PUBLICATIONS

"Narp and NP1 Form Fleterocomplexes that Function in Developmental and Activity-Dependent Synaptic Plasticity", Neuron, Xu, Desheng et al. (Jul. 31, 2003) 39, 513-528.
"NPTX2 and cognitive dysfunction in Alzheimer's Disease", eLlife, Xiao, Mei-Fang et al. (2017) 6, e23798 (27 pages).
"The soluble extracellular fragment of neuroligin-1 targets Abeta oligomers to the postsynaptic region of excitatory synapses", Biochem. Biophys. Res. Commun., Dinamarca, Margarita C. et al. (2015) 466, 66-71.
"A truncating mutation in Alzheimer's disease inactivates neuroligin-1 synaptic function", Neurobiol. Aging, Tristan-Clavijo, Enriqueta et al. (2015) 36, 3171-3175.
"Interaction of amyloid-beta (Abeta) oligomers with neurexin 2alpha and neuroligin 1 mediates synapse damage and memory loss in mice", J. Biol. Chem., Brito-Moreira, Jordano et al. (2017) 292(18), 7327-7337.
"The ADAS-cog in Alzheimer's disease clinical trials: psychometric evaluation of the sum and its parts", J. Neurol. Neurosurg. Psychiatry, Cano, Stefan J. et al. (2010) 81, 1363-1368.
"Mild cognitive impairment as a diagnostic entity", J. Intern. Med., Petersen, R. C. (2004) 256, 183-194.
"Toward defining the preclinical stages of Alzheimer's disease: Recommendations from the National Institute on Aging-Alzheimer's Association workgroups on diagnostic guidelines for Alzheimer's disease", Alzheimers Dement., Sterling, Reisa A. et al. (May 2011) 7(3), 280-292.
"Research criteria for the diagnosis of Alzheimer's disease: revising the NINCDS-ADRDA criteria", Lancet Neurol., Dubois, Bruno et al. (Aug. 2007) 6, 734-746.
"Cerebrospinal Fluid Biomarker Signature in Alzheimer's Disease Neuroimaging Initiative Subjects", Ann. Neurol., Shaw, Leslie M. et al. (Apro. 2009) 65(4), 403-413.
"Dysfunctionally phosphorylated type 1 insulin receptor substrate in neural-derived blood exosomes of preclinical Alzheimer's disease", Faseb J., Kapogiannis, Dimitrios et al. (2015) 29, 589-596.
"Plasma Extracellular Vesicles Enriched for Neuronal Origin: A Potential Window into Brain Pathologic Processes", Front Neurosci., Mustapic, Maja et al. (May 22, 2017) 11, Article 278 (12 pages).
C. P. Jacob et al.: Alterations in Expression of Glutamatergic Transporters and Receptors in Sporadic Alzheimer's Disease, Journal of Alzheimer's Disease 11 (2007), pp. 97-116, IOS Press.
Edward J. Goetzl et al.: Declining Levels of Functionally Specialized Synaptic Proteins in Plasma Neuronal Exosomes With Progression of Alzheimer's Disease, The FASEB Journal, article fj.201700731R. Published Online Oct. 12, 2017.
Edward J. Goetzl et al.: Decreased Synaptic Proteins in Neuronal Exosomes of Frontotemporal Dementia and Alzheimer's Disease, The FASEB Journal, article fj.201600816R. Published Online Sep. 6, 2016 with supplemental data.
Charisse N. Winston et al.: Prediction of Conversion From Mild Cognitive Impairment to Dementia With Neuronally Derived Blood Exosome Protein Profile, Elsevier, Alzheimer's & Dementia: Diagnosis, Assessment & Disease Monitoring 3 (2016), pp. 63-72.

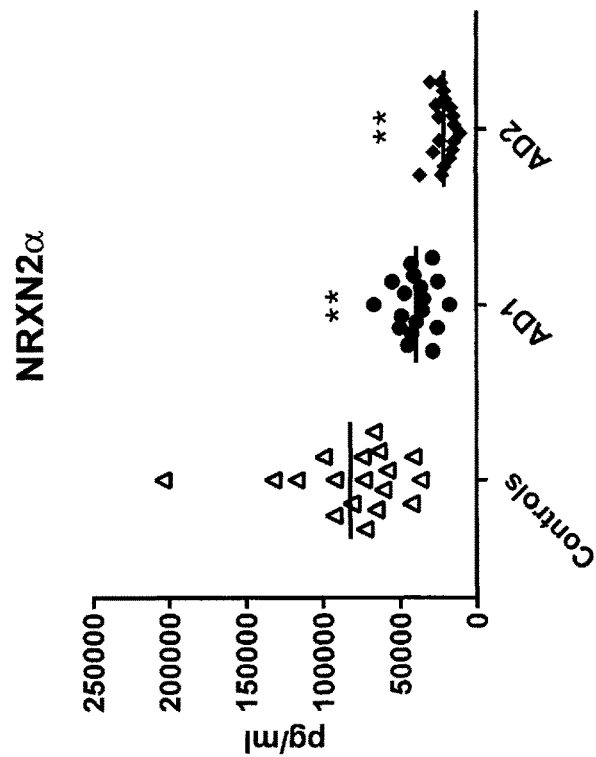
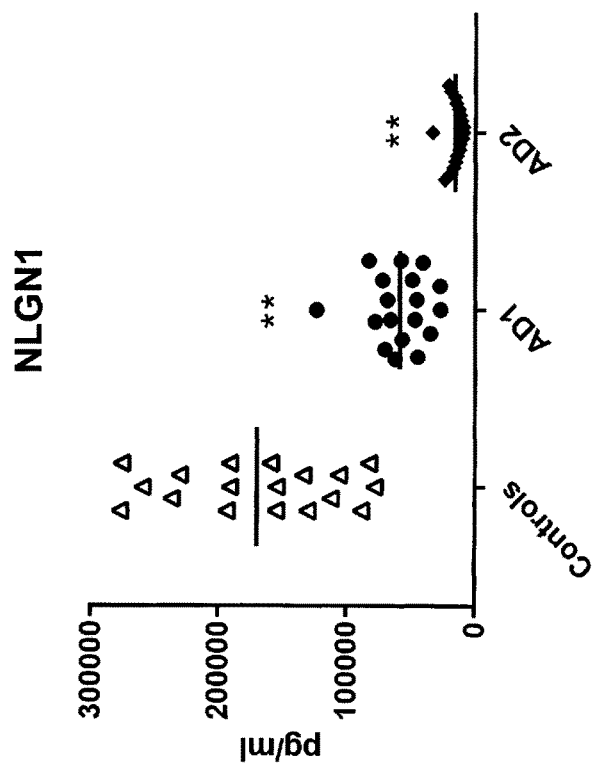
FIG. 4A
FIG. 4B

SPECIALIZED EXCITATORY SYNAPTIC PROTEIN BIOMARKERS OF PLASMA NEURONAL EXOSOMES FOR PREDICTION AND STAGING OF ALZHEIMER'S DISEASE

RELATED APPLICATION

The present application claims benefit of U.S. Provisional Application Ser. No. 62/528,567 filed Jul. 5, 2017 entitled "SPECIALIZED EXCITATORY SYNAPTIC PROTEIN BIOMARKERS OF PLASMA NEURONAL EXOSOMES FOR PREVENTION AND STAGING OF ALZHEIMER'S DISEASE", which is incorporated herein by reference.

FIELD OF INVENTION

The invention is directed to the establishment of an accurate and reliable method for measurement of proteins in human plasma neuron-derived exosomes (NDEs) that are the earliest predictive biomarkers of neurodegeneration in Alzheimer's disease (AD) and the most sensitive staging biomarkers of AD progression.

BACKGROUND OF THE INVENTION

Diminished synaptic function and loss of synapses are characteristic early elements of the neuropathology of AD usually attributed to neuronal deposition of neurotoxic Aβ peptide oligomers in plaques and phosphorylated tau protein in tangles. The distribution and extent of brain synaptic pathology in postmortem brain tissues of patients with AD correlate generally with the severity of premortem cognitive losses. Initial analyses of plasma neuron-derived exosome (NDE) content of several synaptic proteins in patients having AD showed lower levels relative to those of matched control subjects, that were similar to decreases in postmortem AD brain tissues. In cross-sectional studies, AD patient plasma NDE levels of the presynaptic proteins synaptotagmin and synaptophysin, and of the postsynaptic proteins synaptopodin and neurogranin were significantly lower than for control subjects. AD patient plasma NDE levels of the synaptic membrane protein GAP43, however, were only marginally lower than for control subjects. Longitudinal analyses of cargoes in NDEs from plasmas of subjects who were cognitively normal, but would develop definite AD dementia subsequently, showed significantly lower levels of these same synaptic proteins than in plasma NDEs of matched control subjects. Progressive decline of plasma NDE levels of synaptotagmin, synaptopodin and GAP43, but not of synaptophysin or neurogranin, was seen in these AD subjects two to ten years later at the time of diagnosis of AD dementia.

The synaptic proteins investigated initially are widely distributed in central nervous system (CNS) synapses and share functional properties of binding to some other synaptic proteins to form complexes capable of regulating synaptic calcium concentration, and controlling synaptic vesicle fusion, recycling and readily releasable pool size. In relation to the present invention, it has now been determined that two classes of proteins that have essential synaptic maintenance functions restricted to localized excitatory circuits, rather than those of the widely-distributed cluster initially studied, also are present at lower levels in postmortem brain tissues of AD patients, as compared to matched control subjects, and their losses have been seen to contribute directly to the pathogenesis of AD.

SUMMARY OF INVENTION

Neuronal pentraxin 2 (NPTX2) complexes that include neuronal pentraxin 1 (NPTX1) and neuronal pentraxin receptors are expressed presynaptically and secreted by excitatory synapses of pyramidal neurons of the hippocampus and cerebral cortex to then bind specifically with the GluA4 subunit of the postsynaptic AMPA-type glutamate receptors (AMPA4) on fast-spiking parvalbumin interneurons and thereby strengthen or enhance these excitatory synapses. Decreased levels of NPTX2 and correspondingly diminished levels of AMPA4 in brain tissues of AD patients and mice with models of AD are associated with altered pyramidal neuron excitability. Presynaptic neurexin 2α (NRXN2α) and the postsynaptic adhesion protein neuroligin 1 (NLGN1) interact trans-synaptically to ensure structural stability and functions of excitatory synapses in the hippocampus and cerebral cortex. NLGN1 and NRXN2α both bind synaptotoxic Aβ peptide oligomers to increase their synaptic concentrations and thereby enhance oxidative stress and promote synaptic damage in AD. The cognitive losses induced by administration of Aβ peptide oligomers to mice are lessened by concurrent doses of antibodies to NLGN1 and NRXN2α, that diminish binding of amyloid-beta (Abeta) to NLGN1 and NRXN2α.

Significantly lower levels of NPTX2, AMPA4, NLGN1 and NRXN2α were found in plasma neuron-derived exosomes (NDEs) of AD patients as compared to those of matched control subjects. Striking progression of such diminished levels of the four proteins also were found in parallel with progression of indices of diminished cognition from those at a time of normal cognition in pre-clinical AD to those at the time of development of AD dementia. The measuring or quantifying of these levels of NPTX2, AMPA4, NLGN1 and NRXN2α in plasma NDEs allows for early preclinical diagnosis or prediction of AD, as well as tracking of the clinical stage with progression of AD. This is in particular significant in that AD can be diagnosed or predicted prior to overt symptoms of AD in a patient and, thereby, allow for earlier onset of treatment to prevent or delay AD. Early detection is important since currently no cure or means of prevention are known for AD, but treatments are available or becoming available that may delay or slow development of cognitive losses.

BRIEF DESCRIPTION OF THE DRAWINGS

FIGS. 4A-4D show courses of decline in NDE levels of excitatory synaptic protein cargoes with worsening AD. Each point represents the value for a control subject or AD patient and the horizontal line in point clusters is the mean level for that group. Mean±S.E.M. control subject, AD1 (preclinical) patient and AD2 (when dementia was diagnosed) patient values, respectively, are for FIG. 4A 169, 870±15,535, 58,721±5451 and 15,875±1405 pg/ml for NLGN1; for FIG. 4B 81,968±9,306, 39,242±2832 and 21,150±1535 pg/ml for NRXN2α; for FIG. 4C 2210±188, 1476±127 and 686±44.1 pg/ml for AMPA4; and for FIG. 4D 2488±281, 2195±175 and 1330±76.2 pg/ml for NPTX2. The significance of differences between values for control subjects and AD1 patients was calculated by an unpaired Students' t test and for differences between values for AD1 and AD2 patients was calculated by a paired Students' t test; *=p<0.01 and **=p<0.0001.

DETAILED DESCRIPTION OF THE PREFERRED EMBODIMENTS

Figure 1B:
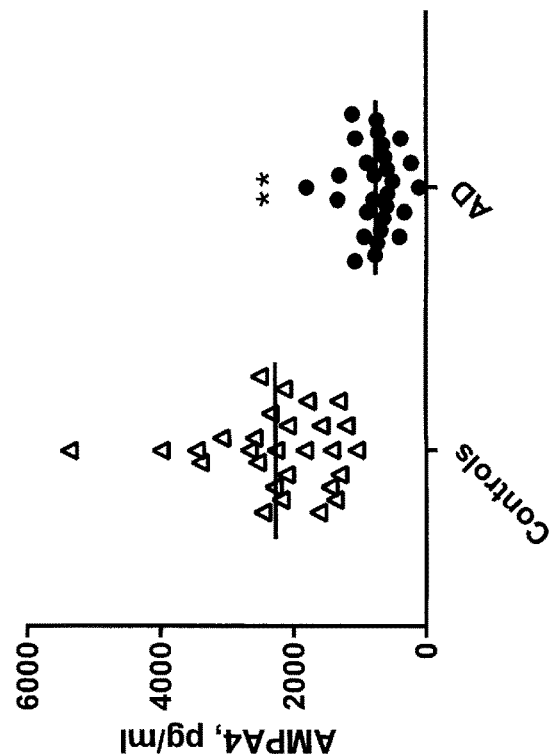
FIGS. 1A and 1B show the NDE levels of AMPA4 (FIG. 1A) and NPTX2 (FIG. 1B) in cross-sectional control and AD groups. Each point represents the value for a control subject or AD patient and the horizontal line in point clusters is the mean level for that group. Mean±S.E.M. (S.E.M.=standard error of the mean) for control subject and AD patient values, respectively, are 2276±180 pg/ml and 766±68.0 pg/ml for AMPA4 and 2656±343 pg/ml and 1250±123 pg/ml for NPTX2. The significance of differences between values for control subjects and AD patients was calculated by an unpaired Students' t test; *=$p<0.01$ and **=$p<0.0001$.
Figure 1A:
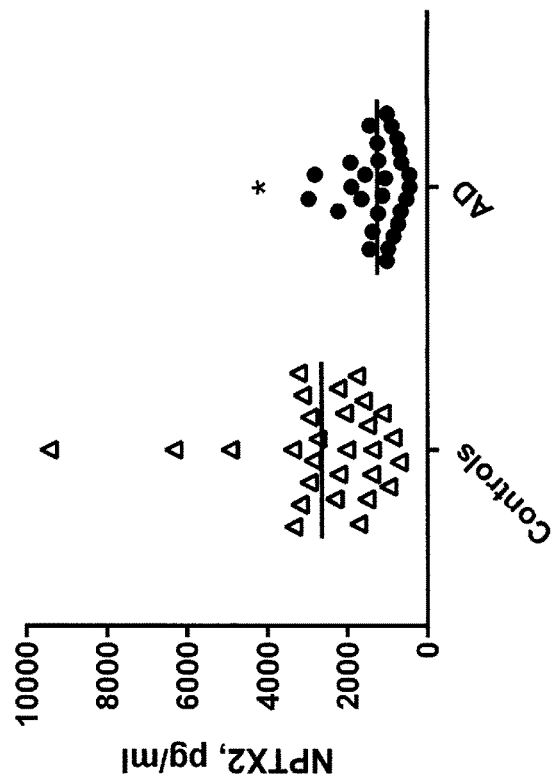
Figure 2A:
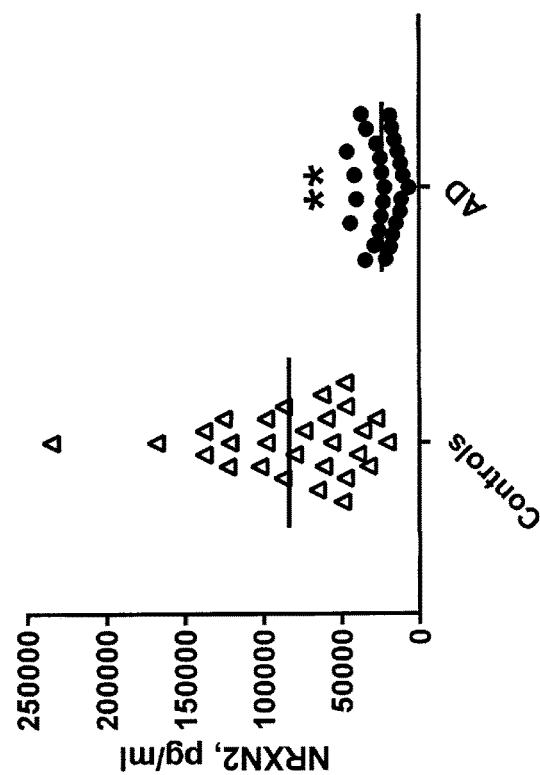
FIGS. 2A and 2B show NDE levels of NLGN1 (FIG. 2A) and NRXN2α (FIG. 2B) in cross-sectional control and AD groups. Each point represents the value for a control subject or AD patient and the horizontal line in point clusters is the mean level for that group. Mean±S.E.M. for control subject and AD patient values, respectively, are 189,498±21,106 pg/ml and 33,155±3305 pg/ml for NLGN1 and 83,374±9132 pg/ml and 23,930±2057 pg/ml for NRXN2α. The significance of differences between values for control subjects and AD patients was calculated by an unpaired Students' t test; **=p<0.0001.
Figure 2B:
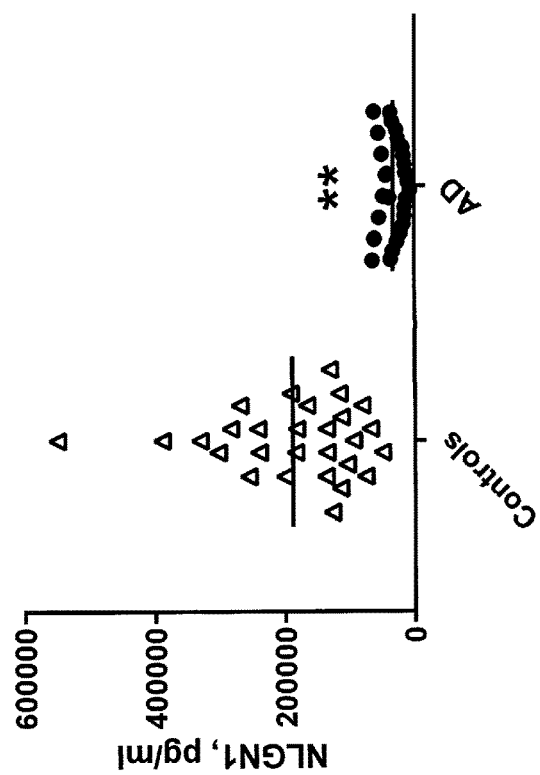

Interactions of presynaptic proteins, neuronal pentraxin 2 (NPTX2) and neurexin2α (NRXN2α) with respective postsynaptic functional partners GluA4-containing glutamate receptor (AMPA4) and neuroligin 1 (NLGN1) enhance or strengthen excitatory synaptic activities in areas of the hippocampus and cerebral cortex. The advantages of the invention involve the quantification of four synaptic protein mediators of selective excitatory neuronal impulses, where decreases in their levels predict very early the risk of development of AD, and permit easy repetitive staging of the severity of the neurodegeneration in AD by a simple blood-based test. As early damage of such excitatory circuits in AD correlates with cognitive losses, plasma neuron-derived exosome (NDE) levels of two pairs of these synaptic proteins are quantified and used as biomarkers for prediction and staging of severity of AD. NDE contents of all four synaptic proteins decrease significantly in AD dementia and diminished levels of AMPA4 and NLGN1 correlate with the extent of cognitive losses (FIGS. 1-3; total number of AD patients in both sets is 46). Prior to the onset of clinically evident dementia, NDE levels of all but NPTX2 are significantly lower than those of matched control subjects (FIG. 4, AD1) and levels of each of these synaptic proteins decline significantly with the development of dementia (FIG. 4, AD2). Reductions in NDE levels of these excitatory synaptic proteins are indicative of the extent of cognitive losses that have occurred and reflect the progression of severity of AD.

Testing and Patient Evaluation.

For the Cross-Sectional studies, 28 patients with early AD were retrospectively identified who had been evaluated extensively in the Clinical Research Unit of the U.S. National Institute on Aging (NIA, Baltimore, Md., USA) and 28 age- and gender-matched cognitively normal control subjects who had donated blood at the Jewish Home of San Francisco (JHSF) in the same time period as the patients (see Table 1(a) below). For the Longitudinal studies described herein, three patients were identified from the University of Kentucky Sanders-Brown Center on Aging and 15 patients from JHSF with moderate AD who had provided blood at two times: first when cognitively intact (AD1 in Table 1(b) below) and, secondly, 5 to 11 years later after diagnosis of dementia (AD2 in Table 1(b) below). Plasmas from 18 cognitively normal control subjects who were age- and gender-matched with the AD1 group were found at JHSF, that had been obtained in the same time period. All plasmas were identified, obtained and stored by the same methods and all plasmas were processed together with the same procedures by the same investigator. Plasmas from patients in the Longitudinal studies were analyzed without knowledge of the clinical data.

TABLE 1

Characteristics of AD Patients and Control Subjects

| Diagnosis | Total Number | Male/Female | Ages (Means ± S.E.M.) | MMSE (Means ± S.E.M.) | ADAS-cog (Means ± S.E.M.) |
|---|---|---|---|---|---|
| (a) Cross-Sectional Sets | | | | | |
| C | 28 | 12/16 | 73.2 ± 1.47 | 29.7 ± 0.13 | 3.32 ± 0.31 |
| AD | 28 | 12/16 | 73.1 ± 1.44 | 25.6 ± 0.83* | 13.7 ± 1.31* |
| (b) Longitudinal Sets | | | | | |
| C | 18 | 10/8 | 70.1 ± 1.66 | 28.3 ± 0.96 | 3.68 ± 0.45 |
| AD1 | 18 | 10/8 | 69.4 ± 1.71 | 28.7 ± 0.47 | 4.19 ± 0.57 |
| AD2 | 18 | 10/8 | 78.2 ± 1.75 | 20.0 ± 1.50* | 17.6 ± 1.64* |

C = Matched control subjects for respective study set.
AD = Patients diagnosed with Alzheimer's disease.
AD1 and AD2 are the groups of AD patients evaluated at two different times in the Longitudinal study, i.e., at a pre-clinical phase (AD1) and after conversion to moderate dementia (AD2), respectively. In the Longitudinal set, C is the control subjects matched to the AD1 patients.
MMSE = Mini-Mental State Examination.
ADAS-cog = AD assessment scale-cognitive subscale.
The significance of differences between cognitive state (MMSE, ADAS-cog) values of the groups were calculated by an unpaired t test for C vs. AD in (a) and for C vs. AD1 in (b), and by a paired t test for AD1 vs. AD2 in (b).
*= p < 0.001.

Patients with AD had mental status testing at the time of each blood sampling. Mini-mental state examination (MMSE) and the AD assessment scale-cognitive subscale (ADAS-cog) were conducted as described in "The ADAS-cog in Alzheimer's disease clinical trials: psychometric evaluation of the sum and its parts", *J. Neurol. Neurosurg. Psychiatry*, Cano, S. J. et al., (2010) 81, 1363-1368 (which in its entirety is incorporated herein by reference). Cross-Sectional study patients from the NIA had amnestic mild cognitive impairment (MCI) or mild dementia from AD with high probability of AD and a Clinical Dementia Rating global score of 0.5 or 1.0 according to the Petersen and Dubois criteria as described in (1) "Mild cognitive impairment as a diagnostic entity", *J. Intern. Med.*, Petersen, R. C. (2004) 256, 183-194 and (2) "Toward defining the preclinical stages of Alzheimer's disease: recommendation from the National Institute on Aging-Alzheimer's Association workgroups on diagnostic guidelines for Alzheimer's disease", *Alzheimer's Dement.*, Sperling, R. A. et al. (2011) 7, 280-292 (each of the above articles (1) and (2) being in its entirety incorporated herein by reference). AD2 patients from JHSF and the University of Kentucky had probable AD and mild-to-moderate dementia by NINCDS-ADRDA criteria and had a Clinical Dementia Rating global score of 1.0 at the time of the second blood collection as described in "Research Criteria for the diagnosis of Alzheimer's disease: revising the NINCDS-ADRDA (National Institute of Neurological and Communicative Disorders and Stroke—Alzheimer's Disease and Related Disorders Association) criteria", *Lancet Neurol.*, Dubois, B. et al. (2007) 6, 734-746 (which in its entirety is incorporated herein by reference). All Cross-Sectional study patients with AD had abnormal cerebrospinal fluid (CSF) levels of amyloid β-peptide (Aβ) 1-42 and P-T181-tau that supported their diagnosis as described in "Cerespinal fluid biomarker signature in Alzheimer's disease neuroimaging initiative subjects", *Ann. Neurol.*, Shaw, L. M. et al. (2009) 65, 403-413 (which in its entirety is incorporated herein by reference).

Blood and CSF sampling of patients and control subjects.

Ten ml of venous blood were drawn into 0.5 ml saline with EDTA (ethylene diamine acetic acid), incubated for 10 min at room temperature, and centrifuged for 15 min at 2500 g. Plasmas were stored in 0.25 ml aliquots at −80° C. CSF levels of P-T181-tau and Aβ 1-42 were quantified by xMAP Technology (Luminex Corp., Austin, Tex., USA) using Inno-Bia AlzBio3 kits (Innogenetics, Ghent, Belgium).

Enrichment of plasma neuron-derived exosomes (NDEs) for extraction and ELISA (enzyme-linked immunosorbent assay) quantification of proteins.

Aliquots of 0.25 ml plasma were incubated with 0.1 ml thromboplastin D (Thermo Fisher Scientific, Waltham, Mass., USA), followed by addition of calcium- and magnesium-free Dulbecco's balanced salt solution with protease inhibitor cocktail (Roche, Indianapolis, Ind., USA) and phosphatase inhibitor cocktail (Thermo Fisher Scientific). After centrifugation at 3000 g for 30 min at 4° C., NDEs were harvested from resultant supernatants by sequential ExoQuick (System Biosciences, Mountain View, Calif., USA) precipitation and immunochemical enrichment with mouse antihuman CD171 (L1CAM neural adhesion protein) biotinylated antibody (clone 5G3; eBiosciences, San Diego, Calif., USA) as described in (1) "Decreased synaptic proteins in neuronal exosomes of frontotemporal dementia and Alzheimer's disease", *Faseb J.*, Goetzl, E. J., et al. (2016) 30, 4141-4148, (2) "Dysfunctionally phosphorylated type 1 insulin receptor substrate in neural-derived blood exosomes of preclinical Alzheimer's disease", *Faseb J.*, Kapogiannis, D., et al. (2015) 29, 589-596, and (3) "Plasma Extracellular Vesicles Enriched for Neuronal Origin: a Potential Window into Brain Pathogenic Processes", *Front. Neurosci.*, Mustapic, M. et al. (2017) 11, 278 (each of the above articles (1), (2) and (3) being in its entirety incorporated herein by reference). M-PER mammalian protein extraction reagent (ThermoFisher Scientific) lysates of NDEs, that contained protease and phosphatase inhibitors, were stored at −80° C.

NDE proteins were quantified by ELISA kits for human tetraspanning exosome marker CD81 (American Research Products—Cusabio, Mass., USA), neuronal pentraxin 2 (NPTX2) and the GluA4 subunit of AMPA-type glutamate receptors (AMPA4) (American Research Products-Cloud Clone Corp.), and neurexin 2α (NRXN2alpha) and neuroligin 1 (NLGN1) (American Research Products-QAYEE-BIO).

The mean value for all determinations of CD81 in each assay group was set at 1.00 and relative values of CD81 for each sample were used to normalize their recovery.

Statistical Analysis.

A Shapiro-Wilks test showed that data in all sets were distributed normally. Statistical significance of differences between means for the Cross-Sectional study groups AD and C, and between the Longitudinal study groups AD1 and C were determined with an unpaired Student's t test, including a Bonferroni correction, and the significance of differences between means for the Longitudinal groups AD1 and AD2 were determined with a paired Student's t test (Prism 6; GraphPad Software, La Jolla, Calif., USA). Relationships between NDE content of a cargo synaptic protein and the corresponding cognitive level of an AD patient were evaluated by Pearson Correlation Coefficients.

Results.

AD patients in the Cross-Sectional study had cognitive scores consistent with mild cognitive impairment or mild dementia that were significantly different from the normal range of scores for the control subjects (see Table 1(a) above). The Longitudinal study subjects evaluated initially at their AD1 pre-clinical phase had normal cognitive scores which were no different than those of their matched control group (see Table 1(b) above). At the time of donation of the second blood sample, the Longitudinal study group was termed AD2 and had mild to moderate dementia and significantly worse cognitive scores than when they were at the AD1 phase.

NDE levels of both synaptic proteins of the two sets were significantly lower than those of the matched control subjects (see FIGS. 1A-1B and FIGS. 2A-2B). Values for the NLGN1-NRXN2α pair were much higher than values for the AMPA4-NPTX2 pair and showed much less overlap with the values of the control subjects. For NLGN1 and NRXN2α, respectively, only four and five control subject values were in the range of those for AD patients (see FIGS. 2A-2B). There were significant inverse correlations between ADAS-cog scores and NDE levels of AMPA4 and NLGN1, but not of NPTX2 or NRXN2α (see FIGS. 3A-3B). Similarly, there were significant positive correlations between MMSE scores and NDE levels of AMPA4 (r=0.621; p=0.0004) and NLGN1 (r=0.525; p=0.0053), but not of NPTX2 or NRXN2α.

For the Longitudinal series of AD patients in the AD1 preclinical phase, NDE levels of AMPA4, NLGN1 and NRXN2α, but not NPTX2, were significantly lower than those of the matched control subjects (see FIGS. 4A-4D). At the AD2 stage of mild to moderate dementia five to 11 years later, NDE levels of all four synaptic proteins had decreased significantly for the group and in every patient compared to their levels at the AD1 phase.

The methods described herein permit quantification of meaningful levels of both members of the two sets of excitatory synaptic proteins and demonstration of significant differences between levels in AD patients and control subjects as well as between pre-clinical and clinically apparent stages of AD (see FIGS. 1A-1B, 2A-2B, and 4A-4D). There are four primary differences between the invention described herein and findings for the group of broadly distributed synaptic proteins described in the "Background of the Invention" above.

The first is distinctive functions in specific excitatory synapses of the hippocampus and areas of the cerebral cortex. Presynaptic complexes that include NPTX2 are secreted into excitatory synapses of pyramidal neurons of the hippocampus and cerebral cortex, bind specifically with the AMPA4 and thereby mediate enhanced synaptic transmission in these circuits. Presynaptic NRXN2α and the postsynaptic adhesion protein NLGN1 interact trans-synaptically in these excitatory synapses of the hippocampus and cerebral cortex to also ensure structural stability and enhanced synaptic functions.

The second distinguishing feature of these two protein pairs is their localization in areas that are affected very early in Aβ where the NRXN2α-NLGN1 pair also may contribute directly to pathogenesis through binding and selective concentration of neurotoxic oligomers of Aβ peptides, such as Aβ1-42 as described in "Interaction of amyloid-beta (Abeta) oligomers with neurexin-2-alpha and neuroligin 1 mediates synapse damage and memory loss in mice", *J. Biol. Chem.*, Brito-Moreira J. et al. (2017) 292, 7327-7337.

Figure 3B:
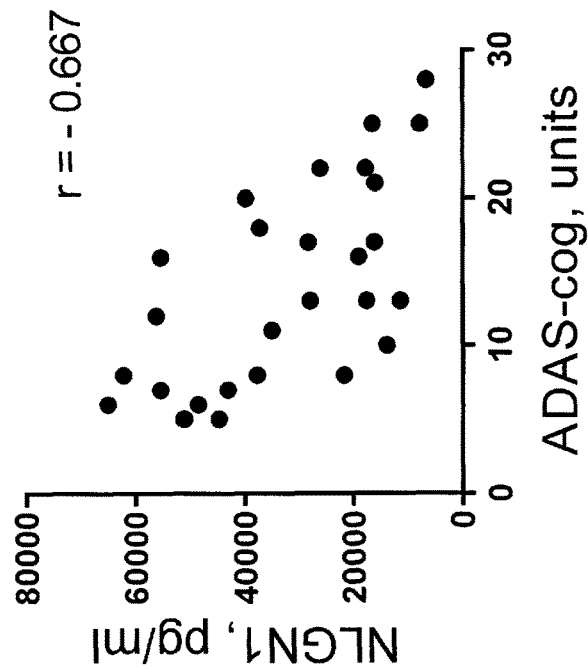
FIGS. 3A and 3B show correlations between NDE contents of excitatory synaptic proteins and cognitive function of AD patients in the cross-sectional set. Each point depicts the levels for one AD patient. The respective p values are 0.0020 for FIG. 3A and 0.0001 for FIG. 3B.
Figure 3A:
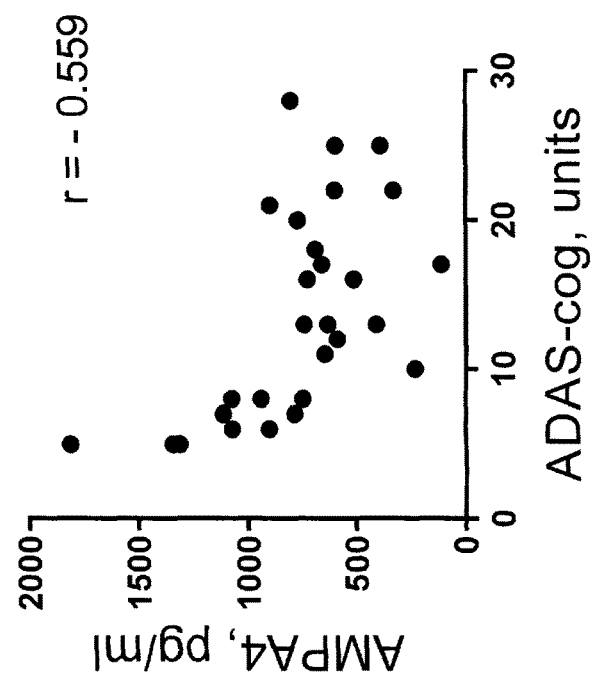
Figure 4D:
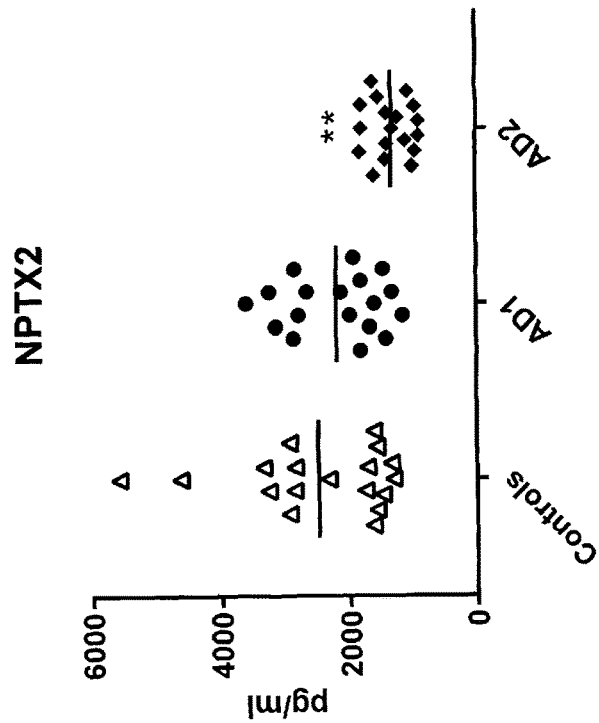
Figure 4C:
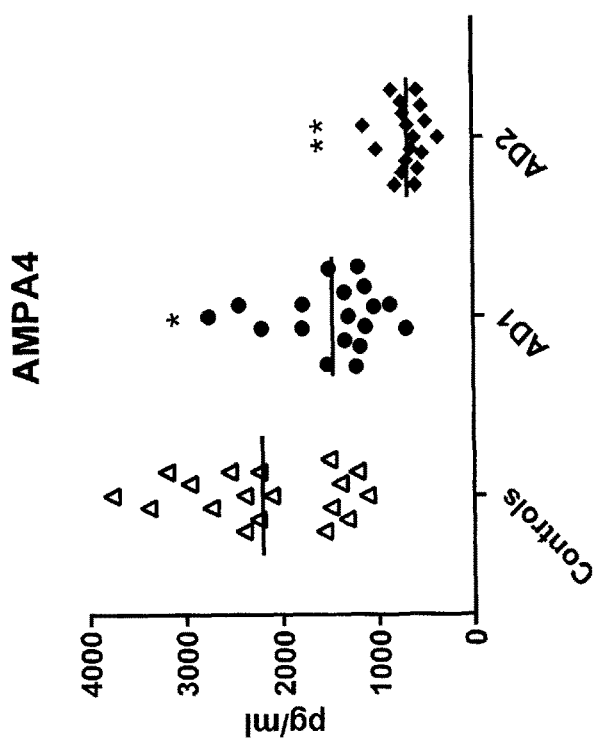

The third difference between two of these functionally excitatory synaptic proteins and numerous other NDE cargo proteins implicated in AD is the correlation between cognitive scores and the levels of AMPA4 and NLGN1 (see FIGS. 3A-3B). This type of correlation, that suggests value for NDE levels of these proteins as staging indicators of AD clinical severity, is shared only by the more broadly distributed synaptic proteins synaptopodin, synaptotagmin and synaptophysin but not by a wide range of other NDE cargo proteins.

Finally, the fourth distinguishing feature of these two synaptic protein pairs is a striking progressive decrease in all of their NDE levels as patient clinical status declines from normal cognition in the pre-clinical stage to dementia with overt AD (see FIGS. 4A-4D). This progressive reduction in NDE level with declining clinical status was seen only for synaptotagmin, GAP43 and to a much lesser extent for synaptopodin, but not for synaptophysin or neurogranin of the more broadly distributed set of synaptic proteins.

Without being bound by theory, diminished NDE levels of cargo proteins may reflect lower neuronal concentrations or less efficient loading of some proteins into NDEs as the disease progresses. There also is potential involvement of greater post-loading proteolysis or distribution in the CNS.

Additional test data is set forth in Table 2 as to a clinical time-course of appearance of AD-associated abnormal proteins in plasma NDEs.

TABLE 2

| Years before dementia | AMPA4 | NPTX2 | NLGN1 | NRXN2α |
|---|---|---|---|---|
| Alzheimer's diagnosis (n = 19) | 681 ± 42.1** | 1324 ± 72.3** | 15,618 ± 1353** | 20,822 ± 1488** |
| 5-8 yrs (n = 19) | 1105 ± 90.8** | 1800 ± 117* | 34,763 ± 2586** | 28,240 ± 1638* |
| 12-14 yrs (n = 14) | 1523 ± 162* | 2144 ± 203* | 63,695 ± 6283* | 52,193 ± 5287* |
| 18-20 yrs (n = 8) | 2051 ± 140** | 2697 ± 274* | 108,147 ± 11,777 † | 61,094 ± 7018$^{ns}$ |
| Healthy controls (n = 19) | 2811 ± 118 | 3698 ± 217 | 166,917 ± 14,988 | 80,305 ± 8958 |

| Years before dementia | P-T181-tau | REST | Synaptophysin | Synaptopodin |
|---|---|---|---|---|
| Alzheimer's diagnosis (n = 19) | 196 ± 4.85* | 96.2 ± 4.01** | 259 ± 21.4** | 1301 ± 76.8** |
| 5-8 yrs (n = 19) | 176 ± 7.57** | 308 ± 18.1** | 3974 ± 542** | 2609 ± 193** |
| 12-14 yrs (n = 14) | 119 ± 6.01* | 576 ± 43.7$^{ns}$ | 9407 ± 590 † | 4838 ± 335$^{ns}$ |
| 18-20 yrs (n = 8) | 83.0 ± 3.99$^{ns}$ | 768 ± 72.1$^{ns}$ | 13,523 ± 994$^{ns}$ | 4522 ± 585$^{ns}$ |
| Healthy controls (n = 19) | 92.0 ± 3.83 | 625 ± 50.6 | 13,070 ± 1190 | 4916 ± 341 |

Table 2 is a clinical time-course of appearance of AD-associated abnormal proteins in plasma NDEs. Each value is the mean pg/ml±S.E.M. in plasma NDE extracts of 19 healthy controls matched by age and sex with 19 patients diagnosed with AD by conventional criteria, and in NDE extracts of 19, 14 and 8 of the same patients from plasmas obtained, respectively, 5 to 8 years, 12 to 14 years and 18 to 20 years before their diagnosis of AD. The level of significance of differences between mean values relative to mean values from the next earlier time period (paired t test) or for the 18 to 20 year group relative to mean values for the matched healthy controls (unpaired t test) are shown by the symbols: $**=p \leq 0.0001$, $*=p \leq 0.01$, $†=p \leq 0.05$ and ns=not significant. AMPA4, GluA4-containing glutamate receptor, NPTX2, neuronal pentraxin 2; NLGN1, neuroligin 1; NRXN2α, neurexin 2α; REST, RE1-silencing transcription factor.

Plasma mean NDE levels of the two pre-synaptic proteins, NPTX2 and NRXN2α, and two post-synaptic proteins, AMPA4 and NLGN1, of human excitatory brain pathways affected in AD are significantly lower at each time point measured than at the earlier time point leading up to the time of clinical diagnosis of AD. For three of the proteins, but not for NRXN2α, the mean NDE level 18 to 20 years before diagnosis of AD is significantly lower than the corresponding NDE level of matched healthy controls. Thus, progressively decreasing plasma NDE levels of these synaptic proteins reflect the increasing severity of preclinical CNS damage by AD, that is already detectable at 18 to 20 years before clinical diagnosis of AD. In contrast, none of the plasma NDE mean levels of the other four recognized biomarkers of AD is distinguished from those of matched healthy controls at 18 to 20 years before clinical diagnosis of AD. Further, only the plasma NDE levels of P-T181-tau and synaptophysin are significantly different at 12 to 14 years than at 18 to 20 years before clinical diagnosis of AD, whereas these differences are significant for all four of the synaptic proteins of the brain excitatory pathways. Thus, these synaptic proteins of human excitatory brain pathways are shown to be the earliest available blood-based biomarkers of pre-clinical AD in living humans. The ability to provide a determination in a living human being of risk or likelihood of AD in the living human being and to determine the progression of AD and cognitive loss is significant for providing early treatment of AD to slow or delay progression of the disease.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. Method of diagnosing and treatment of Alzheimer's Disease (AD) comprising
   (a) obtaining a venous blood sample from a human patient;
   (b) extracting from the venous blood sample synaptic proteins of neuronal pentraxin 2 (NPTX2), GluA4-containing glutamate receptor (AMPA4), neurexin 2α (NRXN2α), and neuroligin 1 (NLGN1),
   (c) determining neuron-derived exosome (NDE) levels for each synaptic pair of (i) NPTX2 and AMPA4 of (b) and (ii) NRXN2α and NLGN1 of (b),
   (d) comparing said NDE levels of each said synaptic pair of (c) with NDE levels of synaptic pairs of (i) NPTX2 and AMPA 4 and (ii) NRXN2α and NLGN1 obtained from the same human patient at a clinically meaningful earlier point in time or obtained, from a control subject known to not have cognitive losses, and detecting a decrease in NDE levels between the compared synaptic pairs; and
   (e) administering to the human patient treatment for AD.

2. The method of claim 1, wherein the NDE levels for said NPTX2, said AMPA4, said NLGN1 and said NRXN2α are each lower than a corresponding synaptic protein of said control subject.

* * * * *